US011154438B2

(12) United States Patent
Hood et al.

(10) Patent No.: US 11,154,438 B2
(45) Date of Patent: Oct. 26, 2021

(54) ABSORBENT ARTICLE WITH AN ABSORBENT CORE HAVING LONGITUDINALLY EXTENDING SIDE REGIONS BEING SPACED APART IN THE TRANSVERSAL DIRECTION BY AT LEAST ONE LONGITUDINALLY EXTENDING CHANNEL REGION, AND METHOD FOR MANUFACTURING SAID ABSORBENT ARTICLE

(71) Applicant: ESSITY HYGIENE AND HEALTH AKTIEBOLAG, Gothenburg (SE)

(72) Inventors: Prelo M. Hood, Philadelphia, PA (US);
Paul Coomes, Philadelphia, PA (US);
Mariela Biber, Newark, DE (US);
Peter Kacenak, Hôrka (SK)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 502 days.

(21) Appl. No.: 15/768,655

(22) PCT Filed: Oct. 20, 2015

(86) PCT No.: PCT/SE2015/051115
§ 371 (c)(1),
(2) Date: Apr. 16, 2018

(87) PCT Pub. No.: WO2017/069666
PCT Pub. Date: Apr. 27, 2017

(65) Prior Publication Data
US 2018/0311081 A1 Nov. 1, 2018

(51) Int. Cl.
*A61F 13/533* (2006.01)
*A61F 13/15* (2006.01)
(Continued)

(52) U.S. Cl.
CPC ...... *A61F 13/533* (2013.01); *A61F 13/15203* (2013.01); *A61F 13/15626* (2013.01);
(Continued)

(58) Field of Classification Search
CPC combination set(s) only.
See application file for complete search history.

(56) References Cited

U.S. PATENT DOCUMENTS 5,451,442 A  9/1995  Pieniak et al.
5,722,967 A  3/1998  Coles
(Continued)

FOREIGN PATENT DOCUMENTS

AU  2014208105 B2  7/2014
CN  1089129 A  7/1994
(Continued)

OTHER PUBLICATIONS

Russian Office Action issued in Russian patent application No. 2018118169 (7 pages) and its English-language translation thereof (6 pages), dated Feb. 19, 2019.
(Continued)

*Primary Examiner* — Michele M Kidwell
(74) *Attorney, Agent, or Firm* — Buchanan Ingersoll & Rooney PC

(57) ABSTRACT

An absorbent article has a longitudinal direction, a transverse direction and a thickness direction, and includes a fluid permeable topsheet, a fluid impermeable backsheet and an absorbent core enclosed between the topsheet and the backsheet having, in the longitudinal direction, a front section, a rear section and a crotch section between the front section and the rear section. The absorbent core has two longitudinally extending side regions being spaced apart in the
(Continued)

transversal direction by at least one longitudinally extending channel region. The channel region is of less basis weight than the side regions.

17 Claims, 6 Drawing Sheets

(51) Int. Cl.
    *A61F 13/47*       (2006.01)
    *B32B 5/02*        (2006.01)
    *B32B 27/32*       (2006.01)
    *A61F 13/56*       (2006.01)
    *A61F 13/45*       (2006.01)
    *A61F 13/53*       (2006.01)

(52) U.S. Cl.
    CPC .......... *A61F 13/4704* (2013.01); *B32B 5/022* (2013.01); *B32B 27/32* (2013.01); *A61F 13/5611* (2013.01); *A61F 2013/15406* (2013.01); *A61F 2013/15422* (2013.01); *A61F 2013/4587* (2013.01); *A61F 2013/4708* (2013.01); *A61F 2013/530007* (2013.01); *A61F 2013/5307* (2013.01); *A61F 2013/530233* (2013.01); *A61F 2013/530343* (2013.01); *B32B 2262/0253* (2013.01); *B32B 2307/726* (2013.01); *B32B 2307/728* (2013.01); *B32B 2307/7265* (2013.01); *B32B 2555/02* (2013.01)

(56) References Cited

U.S. PATENT DOCUMENTS

| | | | |
|---|---|---|---|
| 6,160,197 | A | 12/2000 | Lassen et al. |
| 6,169,223 | B1* | 1/2001 | Mahr ................ A61F 13/00063 602/56 |
| 8,394,316 | B2 | 3/2013 | Alkmin et al. |
| 2002/0123732 | A1* | 9/2002 | Koyama ............ A61F 13/49017 604/385.24 |
| 2004/0044320 | A1* | 3/2004 | Kainth .................... A61L 15/60 604/367 |
| 2004/0087928 | A1 | 5/2004 | Ducker |
| 2004/0267220 | A1 | 12/2004 | Hull et al. |
| 2005/0085783 | A1* | 4/2005 | Komatsu ............. A61F 13/4704 604/385.04 |
| 2007/0078422 | A1 | 4/2007 | Glaug et al. |
| 2007/0299416 | A1* | 12/2007 | Noda ................ A61F 13/15658 604/367 |
| 2010/0036348 | A1 | 2/2010 | De Carvalho et al. |
| 2011/0015602 | A1 | 1/2011 | Schmidt et al. |
| 2011/0130737 | A1* | 6/2011 | Sagisaka ............... A61F 13/533 604/380 |
| 2011/0152813 | A1 | 6/2011 | Ellingson |
| 2013/0289509 | A1 | 10/2013 | Mukai et al. |
| 2015/0359687 | A1 | 12/2015 | Goda et al. |
| 2017/0233909 | A1* | 8/2017 | Wright .................. D04H 1/498 428/172 |
| 2018/0303680 | A1 | 10/2018 | Hood et al. |

FOREIGN PATENT DOCUMENTS

| | | |
|---|---|---|
| CN | 1121432 A | 5/1996 |
| CN | 1609322 A | 4/2005 |
| CN | 102440870 A | 5/2012 |
| CN | 103237532 A | 8/2013 |
| CN | 103269669 A | 8/2013 |
| EP | 0589102 A1 | 3/1994 |
| EP | 2417952 A1 | 2/2012 |
| EP | 2656826 A1 | 10/2013 |
| JP | H08-501473 A | 2/1996 |
| JP | 2006-116036 A | 5/2006 |
| JP | 2006-521166 A | 9/2006 |
| JP | 2010-273842 A | 12/2010 |
| RU | 2290154-02 | 12/2006 |
| RU | 2560916 C2 | 8/2015 |
| TW | 201529055 A | 8/2015 |
| WO | WO-94/06386 A1 | 3/1994 |
| WO | WO-2004/084784 A1 | 10/2004 |
| WO | WO-2006/068549 A1 | 6/2006 |
| WO | WO-2012/086487 A1 | 6/2012 |
| WO | WO-2014/112590 A1 | 7/2014 |
| WO | WO-2015/087680 A1 | 6/2015 |

OTHER PUBLICATIONS

Examination report No. 1 issued in Australian patent application No. 2015412560, dated Jul. 10, 2018.
Japanese Office Action issued in Japanese patent application No. 2018-520509, dated Jun. 1, 2020.
First Chinese Office Action issued in Chinese patent application No. 201580085419.4, dated May 12, 2020.
Japanese Office Action issued in Japanese patent application No. 2018-520508, dated Jun. 8, 2020.
First Chinese Office Action issued in Chinese patent application No. 201580085003.2, dated May 27, 2020.
Examination Report No. 1 issued in Australian patent application No. 2015412559, dated Jul. 18, 2018.
Office Action (Notification of the Second Office Action) dated Dec. 4, 2020, by the Chinese Patent Office in corresponding Chinese Patent Application No. 201580085003.2, and an English Translation of the Office Action. (12 pages).
Office Action (Decision of Rejection) dated May 11, 2021, by the Chinese Patent Office in corresponding Chinese Patent Application No. 201580085003.2, and an English Translation of the Office Action. (12 pages).
Office Action (Second Office Action) dated Jan. 7, 2021, by the Chinese Patent Office in corresponding Chinese Patent Application No. 201580085419.4, and an English Translation of the Office Action. (23 pages).
Office Action (Restriction) dated Jun. 25, 2020, by the U.S. Patent and Trademark Office in co-pending U.S. Appl. No. 15/768,638.
Office Action (Rejection) dated Dec. 3, 2020, by the U.S. Patent and Trademark Office in co-pending U.S. Appl. No. 15/768,638.
Office Action (Decision of Rejection) dated Apr. 6, 2021, by the Chinese Patent Office in Chinese Patent Application No. 201580085419. 4, and an English Translation of the Office Action. (25 pages).
Office Action issued in corresponding U.S. Appl. No. 15/768,638, dated Apr. 2, 2021, (23 pages).
Russian Office Action issued in Russian patent application No. 2018117497, dated Feb. 19, 2019.
Extended European search report issued in European patent application No. 15906801.4, dated Mar. 8, 2019.
Notice of acceptance for patent application issued in Australian patent application No. 2015412560, dated Feb. 28, 2019.
U.S. Appl. No. 15/768,638, Prelo Hood et al.
International Preliminary Report on Patentability issued in International application No. PCT/SE2015/051115, dated Jul. 2, 2018.
Colombian Office Action Oficio N° 4887 dated Jun. 18, 2019 issued in Colombian patent application No. NC2018/0005006 (10 pages) and its English-language translation thereof (6 pages).
English-language translation of Brazilian Search Report and Written Opinion issued in Brazilian patent application No. BR112018007930-8, dated Mar. 14, 2020.
English-language translation of Brazilian Search Report and Written Opinion issued in Brazilian patent application No. BR112018007940-5, dated Mar. 14, 2020.
Colombian Office Action Oficion N° 1132 dated Jan. 22, 2020 issued in Colombian patent application No. NC2018/0005006 (11 pages) and its English-language translation thereof (7 pages).
Japanese Office Action issued in Japanese patent application No. 2018-520508, dated Aug. 26, 2019.
Japanese Office Action issued in Japanese patent application No. 2018-520509, dated Aug. 26, 2019.

(56) References Cited

OTHER PUBLICATIONS

Colombian Office Action Oficio N° 4950 dated Jun. 19, 2019 issued in Colombian patent application No. NC2018/0004335 (16 pages) and its English-language translation thereof (7 pages).

* cited by examiner

ABSORBENT ARTICLE WITH AN ABSORBENT CORE HAVING LONGITUDINALLY EXTENDING SIDE REGIONS BEING SPACED APART IN THE TRANSVERSAL DIRECTION BY AT LEAST ONE LONGITUDINALLY EXTENDING CHANNEL REGION, AND METHOD FOR MANUFACTURING SAID ABSORBENT ARTICLE

CROSS-REFERENCE TO PRIOR APPLICATION

This application is a § 371 National Stage Application of PCT International Application No. PCT/SE2015/051115 filed Oct. 20, 2015, which is incorporated herein in its entirety.

TECHNICAL FIELD

The disclosure relates to an absorbent article having a longitudinal direction, a transverse direction and a thickness direction, and including a fluid permeable topsheet, a fluid impermeable backsheet and an absorbent core enclosed between the topsheet and the backsheet having, in the longitudinal direction, a front section, a rear section and a crotch section between the front section and the rear section. The absorbent core has two longitudinally extending side regions being spaced apart in the transversal direction by at least one longitudinally extending channel region.

The disclosure also relates to an absorbent core for use in an absorbent article and having two longitudinally extending side regions being spaced apart in a transversal direction by at least one longitudinally extending channel region. The absorbent core also has, in the longitudinal direction, a front section, a rear section and a crotch section between the front section and the rear section.

The disclosure also relates to a method for manufacturing an absorbent core for use in an absorbent article having a longitudinal direction, a transverse direction and a thickness direction. The method includes: providing a fluid permeable topsheet; providing a fluid impermeable backsheet; forming, in an absorbent core, at least one longitudinally extending channel region, thereby defining two longitudinally extending side regions being spaced apart in the transversal direction by said channel region; and enclosing the absorbent core between the topsheet and the backsheet. Also, the absorbent core has, in the longitudinal direction, a front section, a rear section and a crotch section between the front section and the rear section.

BACKGROUND

Absorbent articles, for example in the form of incontinence liners, baby diapers and sanitary napkins, are well known. The general purpose of such absorbent articles is to absorb, distribute and store various types of body exudates, while providing a high level of comfort and sense of dryness to the wearer during use of the absorbent article. Also, the absorbent articles prevent the wearer from getting the clothes soiled by such body exudates.

In particular, it can be noted that absorbent articles in the form of incontinence liners are used to protect a wearer against light urine leakage. Such leakage may occur as a result of, for example, pregnancy or childbirth, or during physical efforts such as running or even laughing, sneezing or coughing. For this reason, it is known to use incontinence liners which are designed with an absorption capacity which is sufficient in order to absorb the fluid that is expected to be released into the absorbent article when it is worn.

As regards incontinence liners, there exist certain requirements for such type of products. Initially, it should be noted that an incontinence liner should be designed so as to be worn inside a user's ordinary underwear and to provide protection against light urine leakage. For this reason, an incontinence liner of known type is shaped to provide an optimal fit to the user's undergarment and body and also to absorb leaks of urine during use. To this end, the liner includes a core of absorbent material arranged along a longitudinal axis of the product. Also, the liner normally includes a soft topsheet in order to give the wearer a feeling of freshness and dryness. Furthermore, an incontinence liner should be relatively thin and should be designed with a discreet shape so that it is generally not visible through the wearer's clothes during use. Finally, a liner is normally provided with suitable adhesive means, allowing it to be attached to the wearer's underwear.

In particular, it is noted that an incontinence liner should provide softness, pliability and comfort in addition to absorption of urine.

The patent document US 2007/078422 discloses an absorbent article in the form of a diaper which includes a topsheet and a backsheet which enclose an absorbent core. The absorbent core includes two longitudinally extending gaps extending through the thickness of the core and together defining a longitudinally extending central region between the gaps and two longitudinally extending side regions outside the gaps. Consequently, the central region and the side regions are spaced apart in the transversal direction of the absorbent article by longitudinally gaps extending along the core. The purpose of the article according to US 2007/078422 is to provide an absorbent article which is configured so as to provide a controlled deformation of the article during use.

Although the article disclosed in US 2007/078422 is suitable to be used as a diaper and can provide a controlled deformation during use, there is a need for further improvements. In particular, there is a need for improving the pliability of an incontinence liner, which is a particular type of absorbent article.

SUMMARY

In accordance with the disclosure, there is provided an absorbent article which in particular, but not exclusively, is intended to be used as an incontinence liner and in which properties relating to pliability of the article and the ability to conform to the wearer's anatomy during use are improved in relation to previously known absorbent articles.

As used herein, the term "pliability" means that the liner is designed so that it is easily bent and shaped so as to follow the anatomy of the wearer during use. In particular, the liner is designed so that it bends along its longitudinal direction so as to offer optimal function and fit.

In accordance with the disclosure is an absorbent article having a longitudinal direction, a transverse direction and a thickness direction, and including a fluid permeable topsheet, a fluid impermeable backsheet and an absorbent core enclosed between the topsheet and the backsheet having, in the longitudinal direction, a front section, a rear section and a crotch section between the front section and the rear section. The absorbent core has two longitudinally extending side regions being spaced apart in the transversal direction by at least one longitudinally extending channel region. Also, the channel region is of less basis weight than the side regions.

According to one embodiment, the channel region extends along the entire length of the absorbent core.

As mentioned, the absorbent article provides a high degree of pliability due to the fact that the absorbent core is designed with at least one channel region having a lower basis weight, i.e. less absorbent material per square area (gsm), than the remaining parts of the absorbent core.

The absorbent article has an elongate and generally rectangular shape including a front section, a rear section, and a crotch section between the front section and the rear section. The word "generally" in this context means that, for instance, the corners of the absorbent article may be rounded. The width of the central region in the transversal direction is less than the width of each of the side regions in the transversal direction, at least in the rear section and the front section. However, the rounded rear end corners and the rounded front end corners are not included in the rear section and the front section.

According to one embodiment, the channel region(s) has also less density than the side regions of the absorbent core. The density is measured with an applied pressure of 0.5 kPa.

According to one embodiment, the channel region(s) with the light basis weight areas is of generally the same thickness as the side regions of the core and the central region. Since the channel region with the light basis weight area is of generally the same thickness as the side regions of the core, the channel region has, according to this embodiment, also less density than the side regions of the absorbent core. The density is measured with an applied pressure of 0.5 kPa. This means that, during use, the article will present a high degree of pliability along the direction of the channel region and a high degree of conformity to the anatomy of the wearer. This is an advantage as regards the comfort and the function of the absorbent article.

According to one embodiment, the ratio of the basis weight between the channel region and the remaining part of the absorbent core is at least 2:3, or at least 2:5 or at least 1:2.

According to one embodiment, the ratio of the basis weight between the channel region and the remaining part of the absorbent core is between 1:3 to 2:3.

According to a further embodiment, the ratio of the basis weight between the channel region and the remaining part of the absorbent core is approximately 1:2.

According to one embodiment, the basis weight of the side regions is 250-600 gsm or 250-450 gsm. If the absorbent core also has a central region, the central region may have a basis weight of 250-600 gsm or 250-450 gsm.

According to an embodiment, the article has a single absorbent core. By having a single absorbent core, a thin, compact absorbent product which is comfortable and discreet for the wearer is provided.

According to an embodiment, the article is an incontinence protector, such as, for example, an incontinence liner.

Furthermore, according to an embodiment, the absorbent article comprises includes an acquisition layer generally covering said absorbent core. Such a layer is particularly suitable for use in an incontinence article since a rapid inlet and distribution of fluid is obtained. This means that the acquisition layer is advantageous in situations involving a discharge of a relatively high volume of fluid in a relatively short time. According to an embodiment, the basis weight of the acquisition layer is 30 to 60 gsm, or 40 to 50 gsm.

According to an embodiment, the acquisition layer is a fiber based layer, which for example is a through air bonded nonwoven.

According to one embodiment, the acquisition layer consists essentially of non-absorbent fibers, such as for example thermoplastic polymeric fibers selected from polyolefines, polyesters, polyamides, and blends and combinations thereof.

According to an embodiment, the topsheet also a nonwoven, for example spunbond nonwoven, carded thermobonded nonwoven, carded through air bonded nonwoven or spunlace nonwoven.

According to an embodiment, the absorbent core includes superabsorbent material, which is generally equally distributed along the absorbent core. More precisely, the amount of said superabsorbent material in said absorbent core is within the interval 25-55%, or 35-50%, of the total weight of the absorbent core.

According to an embodiment, the width of said channel region is less than 0.4 times the width of a corresponding side region, at least in the front and back section. According to a further embodiment, the width of said channel region is less than 0.4 times the width of a corresponding side region also in the crotch section.

According to a further embodiment, the width of said channel region is less than 0.1 times the width of the absorbent core at its most narrow region.

Furthermore, according to an embodiment, the channel region is generally parallel and straight along a longitudinal axis of the absorbent article.

According to an embodiment, the absorbent article includes two or more longitudinally extending channel regions. In such case, absorbent core defines two longitudinally extending side regions and a longitudinally extending central region between said side regions, the central region and the side regions being spaced apart in the transversal direction by said channel regions. In a particular embodiment, the channel regions are then generally parallel and straight along the longitudinal direction of the absorbent article. In this manner, optimal properties regarding the pliability of the article can be obtained.

According to one embodiment, the width of each side region is approximately the same as the width of the central region at its most narrow region.

According to a further embodiment, the width of each side region is greater than the width of the central region at its most narrow region.

According to a further embodiment, the central region has, in the crotch section, a width that is less than ⅔ of the total width of the absorbent core in the crotch section, or less than ⅓ of the total width of the absorbent core in the crotch section or less than ¼ of the total width of the absorbent core in the crotch section.

According to an embodiment, the absorbent article includes two channel regions, wherein the width of each channel region is approximately 2-3 millimeters.

According to one embodiment, the width of the central region is 6-12 mm, 7-10 mm or 8-9 mm.

According to one embodiment, the material of the absorbent core of the same type in the side regions and also in the central region (if the core has a central region), but there is however less material per square area in the channel region as compared to the other areas of the core. The absorbent core may be a single continuous layer.

Further disclosed is an absorbent core for use in an absorbent article and having two longitudinally extending side regions being spaced apart in a transversal direction by at least one longitudinally extending channel region, said absorbent core also having, in the longitudinal direction, a front section, a rear section and a crotch section between the front section and the rear section. Also, the channel region is of less basis weight than the side regions.

Also disclosed is a method for manufacturing an absorbent core for use in an absorbent article having a longitudinal direction, a transverse direction and a thickness direction, said method including: providing a fluid permeable topsheet; providing a fluid impermeable backsheet; forming, in an absorbent core, at least one longitudinally extending channel region, thereby defining two longitudinally extending side regions being spaced apart in the transversal direction by said channel region; and enclosing the absorbent core between the topsheet and the backsheet, wherein said absorbent core has, in the longitudinal direction, a front section, a rear section and a crotch section between the front section and the rear section. Furthermore, the method includes forming said channel region with less basis weight than the side regions.

BRIEF DESCRIPTION OF THE DRAWINGS

Embodiments of the invention will be described in greater detail below with reference to the figures shown in the appended drawings.

DETAILED DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 1:
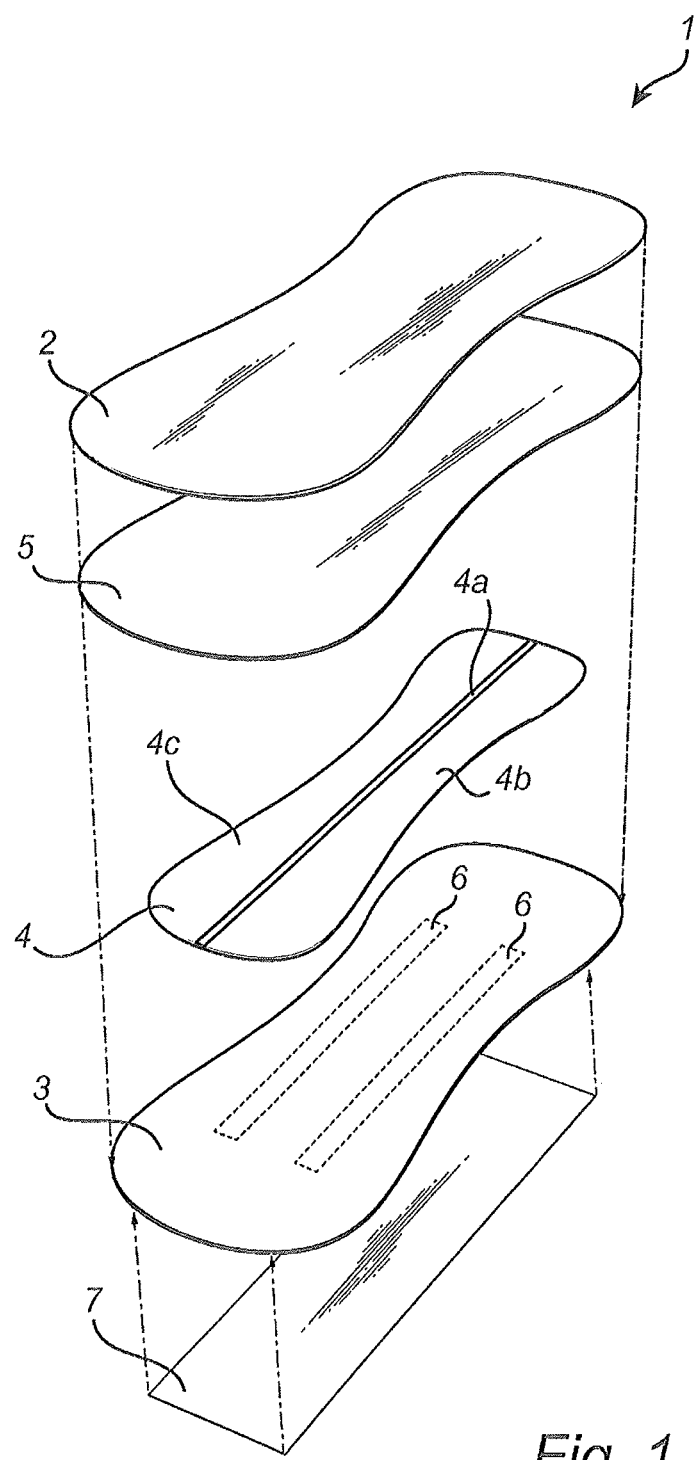
FIG. 1 shows an exploded view of a number of layers forming part of an absorbent article.

With initial reference to FIG. 1, there is shown an exploded view of a personal care absorbent article 1. According to an embodiment, the absorbent article 1 is an incontinence liner, i.e. an incontinence protector article which is specifically designed and optimized so as to absorb light urine leakage.

However, it is to be understood that the principles of the present invention are equally applicable to any type of hygienic absorbent article. Such articles include various types of incontinence liners and pads, and also sanitary napkins, menstrual pads, panty liners or similar products which are worn inside a supporting panty or a holder. Such articles also include baby diapers, pant diapers, training pants, belted diapers or similar disposable absorbent garments.

FIG. 1 shows an incontinence liner 1 with certain layers which together form the complete liner 1. More precisely, the incontinence liner 1 includes a fluid permeable topsheet 2 and a fluid impermeable backsheet 3. The liner 1 also includes an absorbent core 4 which is sandwiched between the topsheet 2 and the backsheet 3. The topsheet 2 is arranged at the surface, i.e. the side facing the wearer, of the incontinence liner 1. The backsheet 3 is arranged at the underside of the liner 1, i.e. facing an undergarment of the wearer. Furthermore, the topsheet 2 and the backsheet 3 extend together laterally outside of the absorbent core 4 along the whole circumference of the absorbent core 4. The topsheet 2, backsheet 3 and the absorbent core 4 may be made of any material suitable for the particular purpose, as discussed in further detail below.

Furthermore, an acquisition layer 5 is situated between the topsheet 2 and the absorbent core 4. The acquisition layer 5 functions as a liquid inlet layer which is arranged on top of the absorbent core 4 and which is especially suitable for use in an absorbent article in the form of an incontinence liner. This is due to the fact that incontinence liners are normally used in situations where there is a discharge of a relatively high volume of fluid in a relatively short time.

The components in the liner 1 may be connected to each other by conventional means such as by means of an adhesive, heat bonding or ultrasonic bonding.

The various layers 2, 3, 4, 5 which form part of the absorbent article 1 will now be described more in detail, with reference primarily to FIGS. 1 and 2.

According to an embodiment, topsheet 2 is formed by a fluid permeable nonwoven fabric or film which is made of thermoplastic synthetic fibers. The topsheet 2 is sufficiently fluid permeable to allow discharged body fluids such as urine to penetrate through the thickness of the topsheet 2 and then reach the acquisition layer 5 and the absorbent core 4 so as to be absorbed. Also, the topsheet 2 is manufactured from a material which is compliant and soft-feeling to the skin of the wearer.

According to further embodiments, the topsheet may be manufactured from various web materials such as woven and nonwoven webs and films, foams, or combinations of the above-mentioned materials. The nonwoven materials to be used for the topsheet 2 may be for example spunbond nonwoven, carded resin bonded materials, carded through-air bonded materials, hydroentangled materials or thermo-bonded materials.

According to further embodiments, the topsheet 2 may be perforated, i.e. may be provided with fluid permeable apertures, and may optionally also have elastic properties which allows it to be stretched in any direction. Furthermore, the topsheet 2 extends across generally the entire absorbent article 1. Also, the topsheet 2 may be a single layer, or a combination of two or more layers.

Furthermore, the backsheet 3 is, according to an embodiment, constituted by a fluid-impermeable and breathable film of polyethylene. According to various embodiments, the materials which can be used for manufacturing the backsheet 3 include thin and flexible fluid impermeable plastic films, or fluid impermeable nonwoven materials, fluid impermeable foams and fluid impermeable laminates.

According to the embodiment shown in the drawings, the backsheet 3 is formed by a single layer, but can alternatively be formed by a multi-layered structure, i.e. a laminate, wherein at least one layer is fluid impermeable. Furthermore, the backsheet 3 can optionally be elastic in either direction. Also, backsheet materials that are not fully fluid impermeable but only resistant to fluid penetration may be used, particularly in cases where relatively small amounts of urine are expected to be absorbed by the incontinence liner 1. According to further embodiments, the backsheet 3 may be breathable, implying that air and vapor may pass through the backsheet. Furthermore, the backsheet 3 may optionally have an outer, garment-facing surface of a textile material such as nonwoven.

Figure 3:
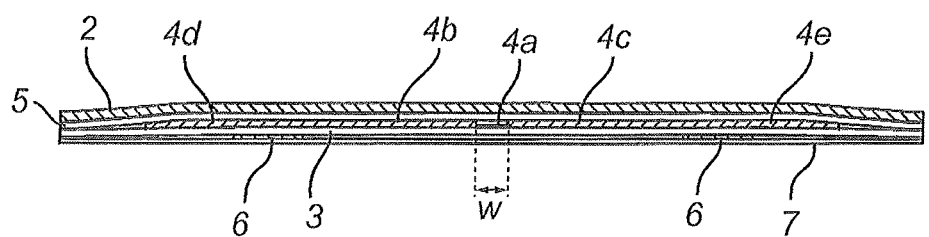
FIG. 3 shows a cross-section through the absorbent article in FIG. 2, as taken along the line III-III in FIG. 2.

As indicated in FIGS. 1 and 3, the rear side of the backsheet 3 is provided with fastening means in the form of adhesive sections 6 (shown with broken lines in FIG. 1) which are covered with a release paper layer 7 when the incontinence liner 1 is in its non-used condition. When the liner 1 is to be used, the release paper layer 7 is removed by the user so that the liner 1 can be fastened to an undergarment.

Furthermore, according to the embodiment shown in the drawings, the incontinence liner 1 includes an absorbent core 4 which is formed by a single layer including fibres of cellulosic fluff pulp and superabsorbent particles. According to alternative embodiments, the absorbent core 4 can be made up of any suitable absorbent or fluid-absorbing material as known in the art, for example foam, fiber waddings and similar materials.

Furthermore, according to an embodiment, the incontinence liner 1 includes an absorbent core 4 which includes a mixture of cellulosic fluff pulp and a suitable amount of superabsorbent particles. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight. According to an embodiment, the amount of said superabsorbent particles corresponds to an amount within the interval 25-55%, or 35-50%, of the total weight of the absorbent core 4.

The superabsorbents are mixed with cellulose fluff pulp so as to form the absorbent core 4. The mixture of cellulose fluff pulp and superabsorbent articles can be homogeneously mixed throughout the entire absorbent core 4.

As mentioned above, the incontinence liner 1 also includes an acquisition layer 5 which functions as a liquid inlet layer and suitably includes synthetic fibers such as polyester or polypropylene and can suitably be manufactured by through-air bonding. According to an embodiment, the acquisition layer 5 is constituted by a 50 gsm through air bonded carded nonwoven material. In a particular embodiment, the acquisition layer 5 is laid directly on top of the absorbent core 4. The acquisition layer 5 is adapted for rapidly acquire and distribute gushes of liquid which may be quickly introduced into the absorbent core 4.

According to further embodiments, the absorbent core 1 may be a homogeneous and continuous structure of the same type of material in a single layer, or may be a layered structure with laminates of the same or different materials.

Figure 2:
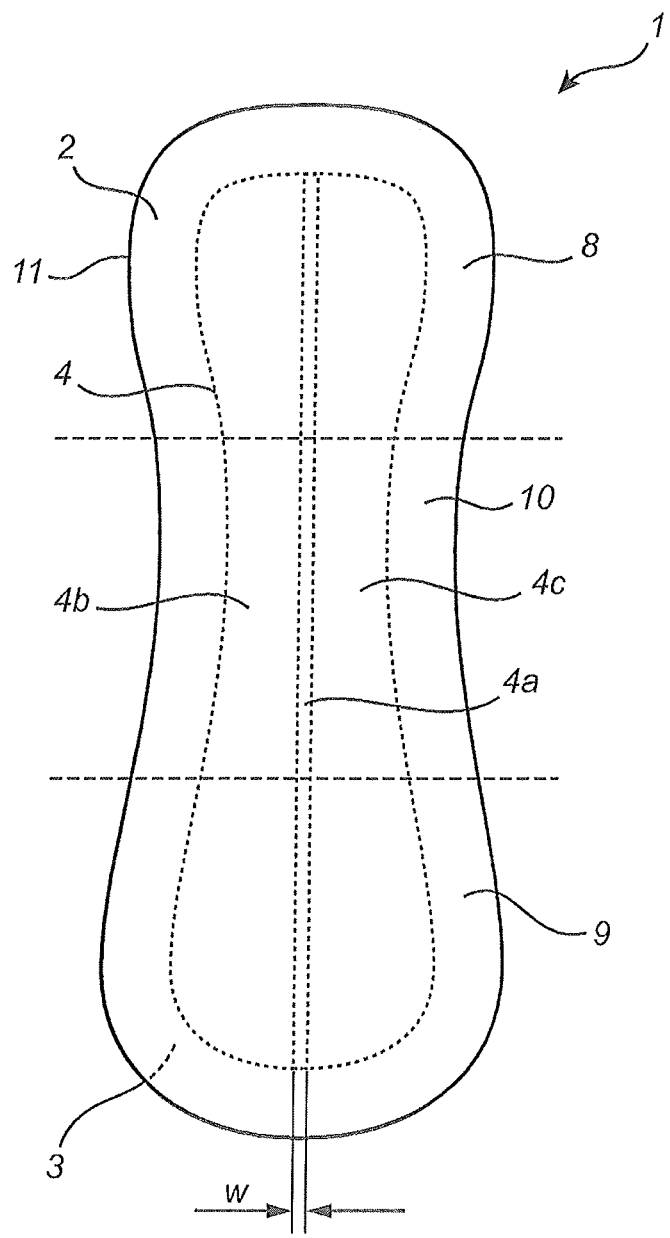
FIG. 2 shows a view of the absorbent article from the side which will be facing a user's undergarment when it is being worn.

FIG. 2 shows a view from the side of the incontinence liner 1 that is intended to be facing towards a wearer's body when the incontinence liner 1 is being worn. It can be seen from FIG. 2 that the incontinence liner 1 according to the embodiment has an elongate and generally rectangular shape including a front section 8, a rear section 9 and a crotch section 10 between the front section 8 and the rear section 9. The word "generally" in this context means that, for instance, the corners of the incontinence protector 1 may be rounded as shown in FIGS. 1 and 2. Furthermore, as shown in FIG. 2, the crotch section 10 defines a waist of the liner 1, i.e. a section of the liner 1 which has slightly less width than the width of the front section 8 and the rear section 9. Also, the crotch section 10 constitutes the main acquisition area for body fluid that reaches the liner 1.

Furthermore, the topsheet 2 and the backsheet 3 are connected to each other in an edge joint 11 around the periphery of the absorbent core 4. Also, the absorbent core 4 is of a size having an area which is slightly smaller than the area of the topsheet 2 and the backsheet 3.

The shape of the incontinence liner 1 as shown in FIGS. 1 and 2 should not be considered limiting to the invention. Accordingly, any other suitable shape may be used, such as hourglass shape, trapezoidal shape, triangular shape an oval shape. The shape of the article may be symmetrical about a transverse centre line through the article, as shown in FIG. 2, or may be asymmetrical with end portions having differing shapes and/or differing sizes. Also, the rear section 9 is intended to be orientated rearwards during use of the liner 1, whereas the front section 8 is intended to be facing forwards towards the abdomen of the wearer during use.

According to an embodiment which is shown in FIGS. 2 and 3 (see also FIG. 1), the absorbent core 4 is formed with a channel region 4*a*, which is in the form of a relatively thin line along the longitudinal direction of the absorbent core 4 and which is designed in a particular manner, as will be described below. Furthermore, a first side region 4*b* and a second side region 4*c* are also defined as longitudinally extending regions on the outside of the channel region 4*a*.

According to the embodiment shown in the drawings, the channel region 4*a* is defined by one single, generally straight line, but according to alternative embodiments, may also be of curved shape or other suitable geometry. Furthermore, as shown in FIGS. 2 and 3, the channel region 4*a* extends along the entire length of the absorbent core. Also, although this embodiment, as shown in FIGS. 2 and 3, shows one channel region 4*a* only, it should be noted that the invention is not limited to one single channel region but can also be implemented with two or more such channel regions. This will be described in further detail below.

In summary, the absorbent article 1 according to the disclosed embodiment has a longitudinal direction, a transverse direction and a thickness direction, and includes a fluid permeable topsheet 2, a fluid impermeable backsheet 3 and an absorbent core 4 enclosed between the topsheet 2 and the backsheet 3. Furthermore, the absorbent core 4 has two longitudinally extending side regions 4*b*, 4*c* and a longitudinally extending channel region 4*a*.

Figure 4:
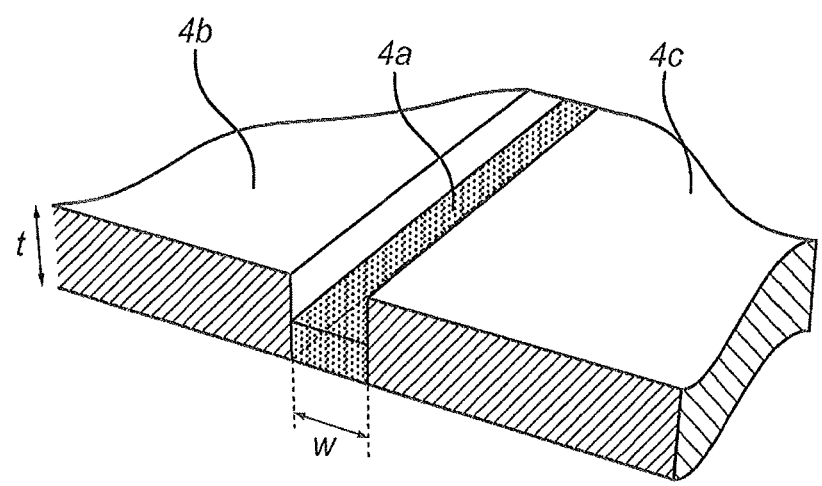
FIG. 4 is an enlarged part of the cross-section through the absorbent core as shown in FIG. 3.

According to an embodiment, and as shown in particular in FIG. 4, the channel region 4*a* is formed with less material (i.e. cellulose fluff pulp, optionally mixed with superabsorbents) than the side regions 4*a*, 4*b*. More precisely, the channel region 4*a* is filled with less material than the remaining part of the core 4, which is implemented by means of a special manufacturing process which will be described in greater detail below. This means that the channel region 4*a* is of less overall (or average) basis weight as compared with the side regions 4*a*, 4*b*, since there is less material in said channel region 4*a*. It could be said that the channel region 4*a* is in the form of a light basis weight area, i.e. an area or section of the absorbent core 4 being formed of material with a relatively low basis weight as regarded relative to the remaining areas of the absorbent core 4. This means that the material of the absorbent core 4 is of the same type both in the channel region 4*a* and the remaining parts of the absorbent core 4, but there is however less material per square area in the channel region 4*a* as compared to the other areas of the core 4.

According to one embodiment, the channel region, during use of the absorbent article, has light basis weight areas of generally the same thickness as the side regions of the core and the central region. Since the channel region with the light basis weight area during this embodiment is of generally the same thickness as the side regions of the core, the channel region has, according to this embodiment, also less density than the side regions of the absorbent core. The density is measured with an applied pressure of 0.5 kPa. This means that the channel region 4a defines a region with less density than the remaining part of the absorbent core 4, i.e. a lower value corresponding to grams of material per square area (gsm), than the remaining parts of the absorbent core 4.

According to an embodiment, a suitable ratio of the basis weight between the channel region 4a and the remaining part of the absorbent core 4 is approximately 1:2.

The purpose of the channel region 4a is to contribute to an increase of the pliability of the absorbent core 4 and the ability for the absorbent article 1 to flex lengthwise. This is an important advantage of the invention.

With reference to FIG. 4, it is noted that the width w of the channel region 4a is approximately 2-3 millimeters. However, variations may occur depending on the design of the absorbent article 1 and the invention is not limited to the above-mentioned dimensions only.

Furthermore, the width w of the channel region 4a is less than 0.4 times the width $w_s$ of a corresponding side region 4b, 4c. Also, the width w of the channel region 4a is less than 0.1 times the width of the absorbent core 4 at its most narrow section, i.e. the crotch section 10.

Furthermore, with reference to FIG. 2, the channel region 4a has a length which is the same as the length of the absorbent core 4 seen in the longitudinal direction. In other words, the channel region 4a extends all the way along the absorbent core 4, i.e. end-to-end between its longitudinal end portions.

As mentioned above, and as shown in FIGS. 1 and 3, the incontinence liner 1 also has fastening means 6 for fastening of the incontinence protector 1 inside a supporting undergarment, such as a pair of underpants (not shown in the drawings). According to an embodiment, the fastening means 6 is in the form of two longitudinally extending strips of adhesive arranged on the rear side, i.e. the garment-facing side, of the backsheet 3.

According to alternative embodiments, the incontinence liner 1 can be provided with various types of fastening means in the form of frictional fasteners, mechanical fasteners such as the hook-and-loop fastener type or combinations of different types of fasteners, as known in the art.

Furthermore, in FIGS. 1 and 2 there is indicated that the fastening means 6 is covered by a releasable protective layer 7. This protective layer may be a siliconized paper, a nonwoven or any other releasable material as is known in the art.

Figure 5:
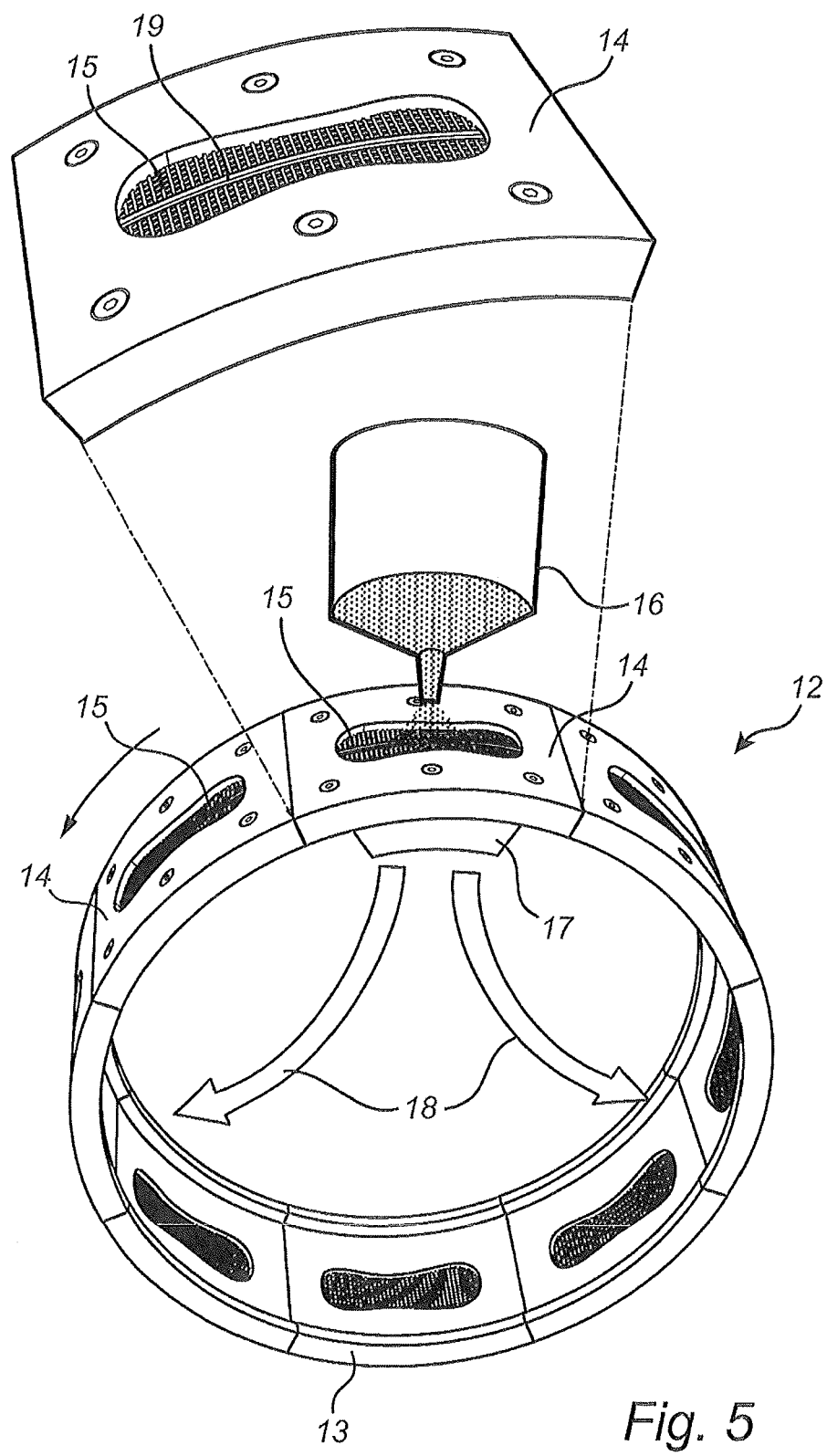
FIG. 5 shows a simplified perspective view of an arrangement for manufacturing the absorbent core.

FIG. 5 shows an arrangement for manufacturing an absorbent core 4 of the type as mentioned as mentioned above. This arrangement is based on a core forming drum 12 which includes a rotating cylinder 13. A number of core molds 14 are arranged along the circumference of the cylinder 13. Each core mold 14 is formed with an internal recess having the form of the finished absorbent core 4 and also has a screen or mesh 15 at its bottom. A supply 16 of the above-mentioned material for the absorbent core 4 (i.e. fibres of cellulosic fluff pulp, optionally mixed with superabsorbents as mentioned above) is arranged above the drum 12 in a manner so that said material fills the core molds 14 as they pass the position of the supply 16 during rotation of the cylinder 13. In order to assist this procedure, a vacuum chamber 17 including a vacuum source is arranged in the cylinder 13 so as to draw air through the core molds 14. This is symbolically indicated by means of arrows 18 in FIG. 5. In this manner, the core molds 14 can be filled with the fluff pulp material.

Furthermore, each core mold 14 is provided with a longitudinally extending narrow portion 19 which corresponds to the position of the above-mentioned channel region 4a forming part of the finished product.

During operation of the arrangement shown in FIG. 5, the fluff pulp material may fill each core mold 14 as it passes the supply 16. According to the embodiment, each core mold 14 has a 3D shape which is arranged so that the light basis weight channel region 4a is formed in each core 4. The complete absorbent core 4, with the channel region 4a having less basis weight than the remaining parts of the core 4, is consequently formed so that when the formed core 4 exits the mold 14, it includes all necessary fluff pulp material including the low basis weight material in the channel region 4a.

Figure 6:
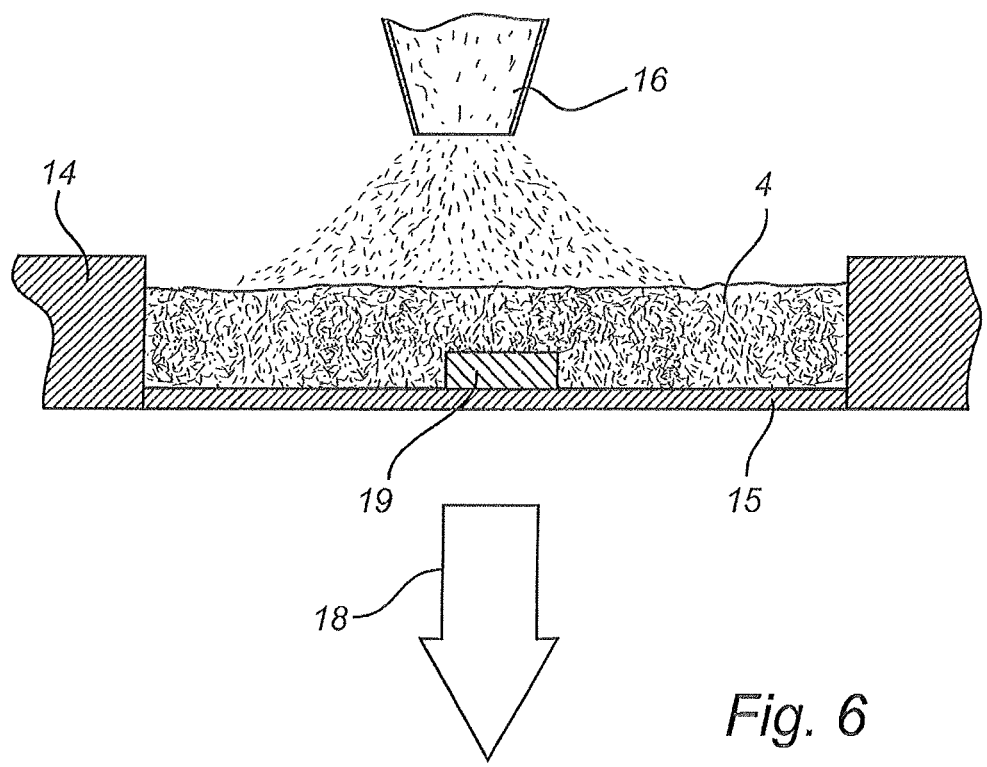
FIG. 6 shows a cross-sectional view of a core mold being used for manufacturing said absorbent core.

FIG. 6 shows a cross-sectional view of a core mold 14, so as to explain the process for manufacturing the absorbent core 4 in greater detail. As mentioned above, the core mold 14 is provided with a screen 15 through which air is drawn, as indicated with an arrow having reference numeral 18. A supply 16 of the fluff pulp material is arranged so that said material is deposited upon the screen 15, as indicated in FIG. 5.

Due to the provision of the longitudinally extending narrow portion 19, no air can be drawn through the core 14 just where this portion 19 is located. Also, no fluff pulp material can be deposited where the portion 19 is located. However, as the layer of fluff pulp material increases in height, fluff pulp material will be deposited on the upper side of said narrow portion 19, i.e. as the absorbent core 4 is gradually being formed.

The final form of the absorbent core 4 when it exits the core forming drum 12 will correspond to that shown in FIG. 4. The upper portion of the channel region 4a in FIG. 4 generally corresponds to the sections of the core mold 14 where the narrow portion 19 is located, i.e. this upper portion is generally free from material. In practical terms however, there may in some cases be a certain amount of material deposited on this upper part of the channel region 4a, which is shown as being empty in FIG. 4. For example, in some cases it can be expected that there will be a certain amount of fluff pulp material deposited also in these sections. So, it may be so that the thickness of the core in the channel region and the side region may be generally the same. However, the basis weight is always less in the channel region compared to the side regions.

In any case, the channel region 4a will have an overall basis weight of material which is less than the remaining parts of the absorbent core 4.

In summary, the channel 4a is formed in the core due to the specifically designed screens 15 and the narrow portion 19, which cause relatively less core material to be deposited in the channel region 4a as compared to the amount of material deposited in other areas of the core 4 (on a grams per square basis). The longitudinally extending narrow portion 19 may have a thickness between 1-3 millimeters, for example 2 mm. The core mold may have a thickness of 3-6, for example 4 mm. By having a thickness of the narrow portion 19 of 0.5 the thickness of the core mold (from top of mold to screen bottom), the basis weight of the channel region will be about 0.5 the basis weight of the side regions.

According to further embodiments, the process shown in FIGS. 5 and 6 for producing the absorbent cores 4 may be followed by a compression step, i.e. wherein the core 4 is pressed together in the thickness direction. This step is generally known as such, and for this reason it is not shown in detail in the drawings.

In summary, an embodiment of the invention is particularly intended to be used as an incontinence liner and includes an absorbent core 4 which has a channel region 4a being of less basis weight than the remaining part of the absorbent core 4.

The invention is not limited to the embodiment but can be varied within the scope of the appended claims. For example, the material and dimensions used for the different layers forming the absorbent article 1 can be varied as indicated above.

According to an embodiment, the absorbent article may include two or more channel regions. In the event that two channel regions are used, they will be formed as two generally parallel lines extending along the entire length of the absorbent core, just as the single channel region extends as shown for example in FIG. 2. In such case, a central region, i.e. generally longitudinally extending area, will be situated between the two channel regions.

Also, in an embodiment including two channel regions, two longitudinally extending side regions will be defined outside each channel region. In other words, the two side regions are spaced apart in the transversal direction by the two longitudinally extending channel regions and the central region between the channel regions. The width of the central region in the transversal direction may be less than the width of each of the side regions in the transversal direction. In a particular embodiment, the width of the two channel regions is approximately 2-3 millimeters, and the width of the central region is approximately 9 millimeters. However, variations may occur depending on the design of the absorbent article.

Furthermore, the channel regions are of less basis weight than the remaining parts of the absorbent core, in a manner which is similar to the embodiment described with reference to FIGS. 1-4.

Test Method for Determining the Pliability of the Absorbent Article

Test Method:

Bending Mode (12-92)—test method for pliability

Summary:

An absorbent article according to an embodiment of the invention and as specified below presents a decrease in product stiffness by at least 25%.

Purpose and Field of Test Application:

The test method is used to define the pliability, stiffness or resistance in a product, when the product is folded or bent in a fixture designed for the purpose. The test method should describe the force that is required to shape a product to match the body after being applied to underwear.

Definition (Force):

The force is defined as the resistance that occurs when the product, which is resting on a Teflon-covered lower fixture, is folded into the fixture by the downward moving metal wires in an upper fixture.

Principle:

The product rests freely on two horizontal, parallel, Teflon-covered supports. The sample is pressed down at the centerline of the product between the two supports using a tensile tester. The maximum force is then registered. A detailed description of the test process will follow below.

Equipment:

| | |
|---|---|
| Tensile testing equipment | such as Lloyd LRX |
| Load cell | 20N |
| Speed | 300 mm/min |
| Crosshead movement | 40 mm |
| Upper fixture | 12-92, produced by Essity Hygiene and Health AB, metal wire with a diameter of 3 mm |
| Lower fixture | 47-07, produced by Essity Hygiene and Health AB, cross-section of the supports is circular with a diameter of 10 mm and the distance between the center of the supports is 40 mm |
| Talc | such as baby powder |
| Teflon tape | PD 420, produced by Stokvis |

Sample Preparation:
1. The fixture should be fitted to the tensile tester.
2. Place product on the lower fixture. The upper fixture should be adjusted leaving a distance between the upper metal and the product. The product should have no contact with the upper fixture before start.
3. Press zero.
4. The release paper on the product should be removed before the test and the adhesive should be covered in talc to remove stickiness.

Procedure:

Place the product on the lower fixture with topsheet facing upwards. Center the product so that the upper fixture meets the product precisely in the center. Press start.

Calculation:

Maximum force should be registered. State the accuracy of the results by 1 decimal unit N.

Figure 8:
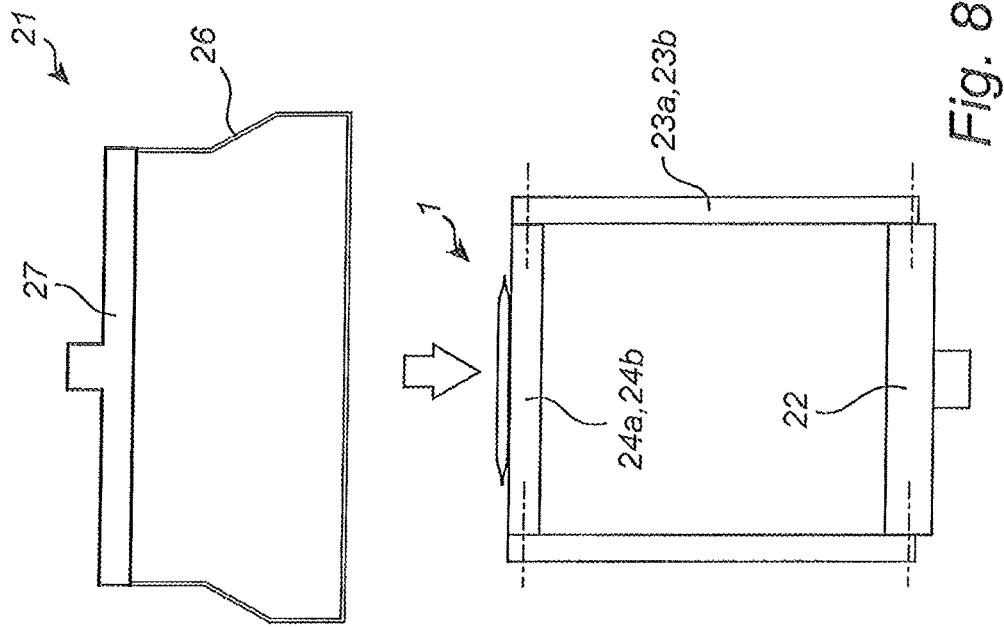
FIG. 8 is a further view of the arrangement for performing a flexural rigidity test.
Figure 7:
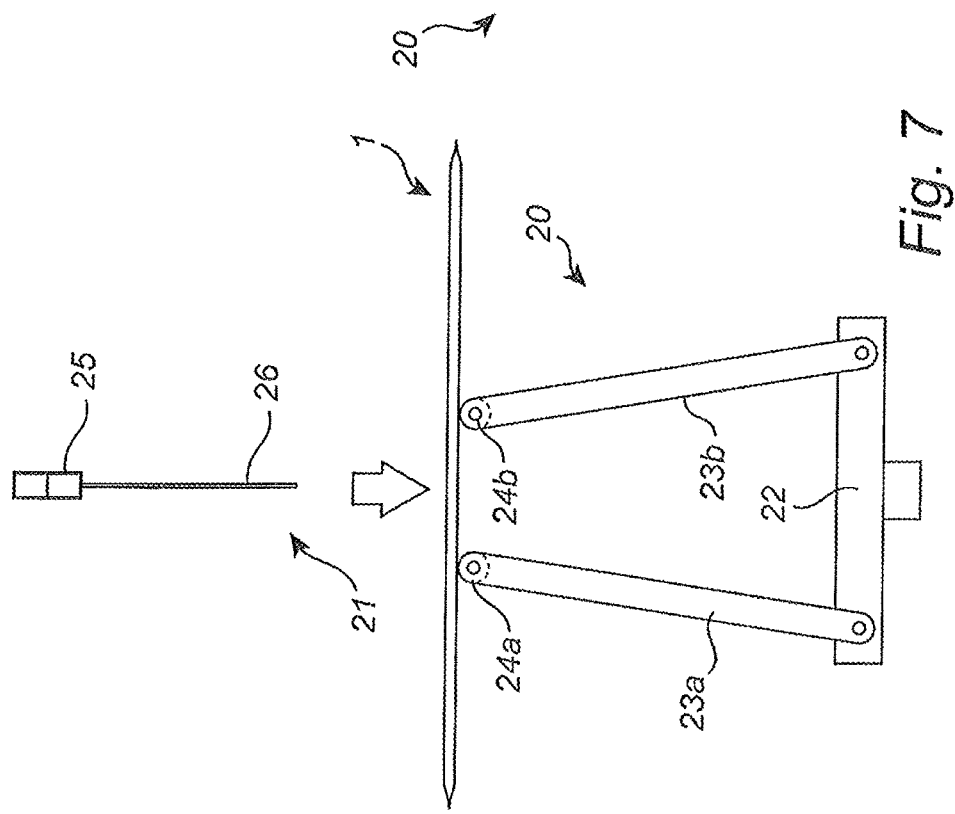
FIG. 7 is a side view of an arrangement for performing a flexural rigidity test of an article.

A more detailed description of the test method will now follow with reference to FIGS. 6 and 7. FIG. 7 is a schematic side view of the equipment used for performing the flexural rigidity test. FIG. 8 is another schematic side view of the equipment, as seen perpendicular to the view of FIG. 7.

The equipment includes a base fixture 20 for supporting an article 1 to be measured, and an upper fixture 21 to be lowered down onto the article 1 when resting on the base fixture 20. The base fixture 20 includes a base means 22 including a holder for attachment to a tensile tester. The base means 22 is provided with two support means 23a and 23b. Each support means 23a, 23b includes two generally vertical bars and two horizontal bars 24a, 24b extending horizontally between the two generally vertical bars. The support means 23a, 23b are attached to the base means 22 in a position so as to lean somewhat towards each other. Hence, the distance between the centre of the support means 23a, 23b at the base means 22 is about 87 mm, and the distance between the centers of the support means 23a, 23b at the horizontal bars 24a, 24b is only 40 mm. The horizontal bars 24a, 24b extend horizontally and in parallel.

The horizontal bars 24a, 24b are covered with Teflon® and have a circular cross-section with a diameter of 10 mm (including the Teflon). The surface of the horizontal bars 24a, 24b is smooth.

The upper fixture 21 includes a holder 25 for attachment to a tensile tester, and a metal wire structure 26. The metal wire structure 26 includes a horizontal portion for contacting the product 1 when lowered towards the base fixture. The horizontal portion has a length of 140 mm. At its two ends, the horizontal portion is attached to vertically extending wire portions, having a length of 50 mm. Thereafter, the wire portions continue with angled wire portions, also having a length of 50 mm, and leaning towards each other such that the upper ends of the angled wire portions are separated by a distance of 90 mm. The angled wire portions are each followed by a second horizontal wire portion having a length of 50 mm. Finally, the second horizontal wire portions are attached to the holder 25. The distance between the second horizontal wire portions at the holder 25 is thus 90 mm. The metal wire 26 has a diameter of 3 mm, and is made of a rigid and inflexible material.

The upper fixture 21 is arranged in relation to the base fixture 20 such that the metal wire structure 26 is generally parallel to the horizontal bars 24a, 24b.

For testing, the fixtures 20, 21 are mounted to the tensile tester. The upper fixture is adjusted such that the distance between the horizontal metal wire and the uppermost side of the sample when resting on the base 22 of the base fixture is about 2 mm. With this distance, the sample may easily be positioned on the base fixture. The sample shall be positioned such that the upper fixture will impact the middle of the sample.

For testing, the upper fixture is lowered towards the sample with a velocity of 200 mm/min, so as to push the product down between the horizontal supports. The test is finished when the entire product has been pushed down between the supports.

Measurement Results:

Table 1 below shows the measurement results for a conventional incontinence liner, whereas Table 2 below shows the measurement results for an incontinence liner in accordance with an embodiment of the present invention. Both test series were based on a procedure involving 25 measurements.

TABLE 1

| No. | Load (N) | No. | Load (N) | No. | Load (N) | No. | Load (N) | No. | Load (N) |
|-----|----------|-----|----------|-----|----------|-----|----------|-----|----------|
| 1   | 1.86486  | 2   | 1.81738  | 3   | 2.39533  | 4   | 1.93933  | 5   | 1.43223  |
| 6   | 1.91535  | 7   | 2.04369  | 8   | 1.67681  | 9   | 1.53327  | 10  | 1.73858  |
| 11  | 1.78109  | 12  | 2.01489  | 13  | 2.43191  | 14  | 1.86583  | 15  | 1.64176  |
| 16  | 1.31981  | 17  | 1.59838  | 18  | 1.84993  | 19  | 1.84104  | 20  | 1.84514  |
| 21  | 1.63777  | 22  | 1.59693  | 23  | 2.28303  | 24  | 2.39323  | 25  | 1.56197  |

TABLE 2

| No. | Load (N) | No. | Load (N) | No. | Load (N) | No. | Load (N) | No. | Load (N) |
|-----|----------|-----|----------|-----|----------|-----|----------|-----|----------|
| 1   | 1.05162  | 2   | 1.14510  | 3   | 1.22609  | 4   | 1.22405  | 5   | 1.82324  |
| 6   | 1.26744  | 7   | 1.23330  | 8   | 1.26420  | 9   | 1.60583  | 10  | 1.26853  |
| 11  | 1.14848  | 12  | 1.52239  | 13  | 1.29964  | 14  | 1.74673  | 15  | 1.46880  |
| 16  | 2.14818  | 17  | 1.20120  | 18  | 1.44238  | 19  | 1.17635  | 20  | 1.14173  |
| 21  | 1.79068  | 22  | 1.19458  | 23  | 1.31233  | 24  | 1.35722  | 25  | 1.36632  |

Conclusion:

In conclusion, it was noted that the mean value for the conventional incontinence liner was 1.8408 N, whereas the mean value for the incontinence liner according to an embodiment of the invention was 1.3771 N. This means that the liner according to the embodiment of the invention has a product stiffness or pliability which is 25.2% less than the conventional liner.

The invention claimed is:

1. An absorbent article having a longitudinal direction, a transverse direction and a thickness direction, having, in the longitudinal direction, a front section, a rear section, and a crotch section between the front section and the rear section, and comprising a fluid permeable topsheet, a fluid impermeable backsheet, and an absorbent core enclosed between the topsheet and the backsheet, wherein the absorbent core comprises superabsorbent material being generally equally distributed along said absorbent core in an amount of 25-55% of the total weight of the absorbent core and has two longitudinally extending side regions and at least one longitudinally extending channel region, the two longitudinally extending side regions being spaced apart in the transversal direction by the at least one longitudinally extending channel region, wherein a ratio between the basis weight of the at least one channel region and the basis weight of the side regions of the absorbent core is between 1:3 and 2:3, and wherein the channel region extends along the entire length of the absorbent core.

2. The absorbent article according to claim 1, wherein the absorbent article is an incontinence liner having a single absorbent core.

3. The absorbent article according to claim 1, further comprising an acquisition layer generally covering said absorbent core.

4. The absorbent article according to claim 1, wherein the absorbent core comprises two or more longitudinally extending channel regions.

5. The absorbent article according to claim 4, wherein the absorbent core has two longitudinally extending side regions and a longitudinally extending central region between said side regions, the central region and the side regions being spaced apart in the transversal direction by said channel regions.

6. The absorbent article according to claim 5, wherein the width of the central region is less than the width of the side regions at least in the front section and the rear section.

7. The absorbent article according to claim 6, wherein the width of the central region in the transversal direction is less than the width of each of the side regions in the transversal direction also in the crotch section.

8. The absorbent article according to claim 4, wherein said channel regions are generally parallel and straight along a longitudinal direction of the absorbent core.

9. The absorbent article according to claim 5, wherein the width of the central region is 6-10 mm.

10. The absorbent article according to claim 1, wherein the width of the at least one channel region is less than 0.4 times the width of a corresponding side region.

11. The absorbent article according to claim 5, wherein the width of each channel region is approximately 2-3 millimeters.

12. The absorbent article according to claim 1, wherein the width of the at least one channel region is less than 0.1 times the width of the absorbent core at a most narrow region of the absorbent core.

13. The absorbent article according to claim 1, wherein the at least one channel region is formed in the core by deposition of core material, said deposition of core material being relatively less in the channel region as compared to the deposition of material in other areas of the core.

14. An absorbent core having a longitudinal direction for use in an absorbent article and having two longitudinally extending side regions and at least one longitudinally extending channel region, the two longitudinally extending side regions being spaced apart in a transversal direction by the at least one longitudinally extending channel region, said absorbent core also having, in the longitudinal direction, a front section, a rear section, and a crotch section between the front section and the rear section, wherein a ratio between the basis weight of the channel region and the basis weight of the side regions of the absorbent core is between 1:3 and 2:3, wherein the at least one channel region extends along the entire length of the absorbent core, and wherein said absorbent core comprises superabsorbent material being generally equally distributed along said absorbent core in an amount of 25-55% of the total weight of the absorbent core.

15. A method for manufacturing an absorbent core for use in an absorbent article having a longitudinal direction, a transverse direction and a thickness direction, said method comprising:

providing a fluid permeable topsheet;

providing a fluid impermeable backsheet;

forming an absorbent core comprising superabsorbent material being generally equally distributed along said absorbent core in an amount of 25-55% of the total weight of the absorbent core having at least one longitudinally extending channel region, thereby defining two longitudinally extending side regions being spaced apart in the transversal direction by said channel region, wherein a ratio between the basis weight of the channel region and the basis weight of the side regions of the absorbent core is between 1:3 and 2:3, and wherein said channel region extends along the entire length of the absorbent core; and enclosing the absorbent core between the topsheet and the backsheet, wherein said absorbent core has, in the longitudinal direction, a front section, a rear section, and a crotch section between the front section and the rear section.

16. The absorbent article according to claim 1, wherein all materials in the absorbent core are homogeneously mixed throughout the absorbent core.

17. The absorbent core according to claim 14, wherein all materials in the absorbent core are homogeneously mixed throughout the absorbent core.

* * * * *